US012566176B2

(12) United States Patent
Capocasale et al.

(10) Patent No.: US 12,566,176 B2
(45) Date of Patent: Mar. 3, 2026

(54) FLOW CYTOMETRY SYSTEM AND METHODS FOR THE DIAGNOSIS OF INFECTIOUS DISEASE

(71) Applicant: FlowMetric Life Sciences, Inc., Doylestown, PA (US)

(72) Inventors: Renold Julius Capocasale, Mount Laurel, NJ (US); Julie Ann Bick, Easton, PA (US)

(73) Assignee: FlowMetric Life Sciences, Inc., Doylestown, PA (US)

( * ) Notice: Subject to any disclaimer, the term of this patent is extended or adjusted under 35 U.S.C. 154(b) by 304 days.

(21) Appl. No.: 18/070,644

(22) Filed: Nov. 29, 2022

(65) Prior Publication Data

US 2023/0160887 A1 May 25, 2023

Related U.S. Application Data

(62) Division of application No. 16/012,369, filed on Jun. 19, 2018, now Pat. No. 11,513,119.

(60) Provisional application No. 62/514,791, filed on Jun. 3, 2017.

(51) Int. Cl.
| | |
|---|---|
| *G01N 33/569* | (2006.01) |
| *G01N 33/50* | (2006.01) |
| *G01N 33/68* | (2006.01) |

(52) U.S. Cl.
CPC ......... *G01N 33/569* (2013.01); *G01N 33/505* (2013.01); *G01N 33/5091* (2013.01); *G01N 33/6863* (2013.01); *G01N 2333/435* (2013.01); *G01N 2333/4703* (2013.01); *G01N 2333/70514* (2013.01); *G01N 2333/70582* (2013.01); *G01N 2333/70596* (2013.01)

(58) Field of Classification Search
CPC .............. G01N 33/569; G01N 33/505; G01N 33/5091; G01N 33/6863
See application file for complete search history.

(56) References Cited

U.S. PATENT DOCUMENTS

| | | | | |
|---|---|---|---|---|
| 2001/0006789 A1* | 7/2001 | Maino | .............. | G01N 33/56972 435/7.2 |
| 2002/0148728 A1* | 10/2002 | Kumar | ............... | G01N 21/6428 204/451 |
| 2007/0178533 A1* | 8/2007 | Poccia | ................. | G01N 33/505 435/7.2 |
| 2008/0206752 A1* | 8/2008 | Balakirev | ........ | G01N 33/54353 435/6.11 |
| 2016/0195529 A1* | 7/2016 | Lalvani | ............ | G01N 33/56966 514/789 |

FOREIGN PATENT DOCUMENTS

| | | |
|---|---|---|
| WO | 2005015207 A2 | 2/2005 |
| WO | 2015033136 A1 | 3/2015 |
| WO | 2015033137 A1 | 3/2015 |

OTHER PUBLICATIONS

International Preliminary Report on Patentability and Written Opinion mailed Dec. 12, 2019 for International Patent Application No. PCT/US2018/038310.
Kumolosasi et al., "Kinetics of Intracellular, Extracellular and Production of Pro-Inflammatory Cytokines in Lipopolysaccharide-Stimulated Human Peripheral Blood Mononuclear Cells", Tropical Journal of Pharmaceutical Research, Apr. 2014, pp. 536-543, vol. 13, No. 4.
Kwak et al., "Intracellular and Extracellular Cytokine Production by Human Mixed Mononuclear Cells in Response to Group B Streptococci", Infection and Immunity, Jan. 2000, pp. 320-327, vol. 68, No. 1.
Lin et al., "Granzyme B Secretion by Human Memory CD4 T Cells is Less Strictly Regulated Compared to Memory CD8 T Cells", BMC Immunology, 2014, pp. 1-15, vol. 15, No. 36.
Zeng et al. "Unique Patterns of surface receptors, cytokine secretion, and immune functions distinguish T cells in the bone marrow from those in the periphery: impact on allogeneic bone marrow transplantation", Blood, 2002, pp. 1449-1457, vol. 99, No. 4.

\* cited by examiner

*Primary Examiner* — Gailene Gabel

(74) *Attorney, Agent, or Firm* — The Webb Law Firm

(57) ABSTRACT

Flow cytometry is used for diagnosis of infectious diseases by an analysis of cell mediated immune responses to specific infective agent antigens. Apparatus and methods of advanced flow cytometry are utilized to detect cell mediated immune responses to the presence of specific antigens from infective agents, such as bacteria, protozoa, viruses, helminth, prions. In some embodiments, methods as provided herein can be utilized in vitro to diagnose multiple infections within individuals.

5 Claims, 13 Drawing Sheets

Total CD71

FLOW CYTOMETRY SYSTEM AND METHODS FOR THE DIAGNOSIS OF INFECTIOUS DISEASE

CROSS-REFERENCE TO RELATED APPLICATIONS

This application is a divisional of U.S. patent application Ser. No. 16/012,369, filed on Jun. 19, 2018, and claims priority to and the benefit of U.S. Provisional Application No. 62/514,791, filed on Jun. 3, 2017, the entire contents and teachings of which are hereby incorporate by reference in their entireties.

FIELD

The present disclosure, relates to methods and systems for diagnosing infectious disease and more particularly to flow cytometry systems and methods for diagnosing infectious disease.

BACKGROUND

Infectious diseases remain a health concern in many regions of the world. Some of these regions are impoverished, or remote, and many of such regions are based on a nomadic population. The mobility of the population makes identifying, tracking and treating infected individuals a major challenge. Lack of a capacity to make appropriate diagnoses and devise appropriate interventions in such regions of the world perpetuate and spread infections.

As one example of a stubborn and problematic infectious disease, tuberculosis (TB) remains a leading cause of death globally, despite the availability of inexpensive and effective short-course therapies. *Mycobacterium tuberculosis* is the causal agent of TB, and appropriate diagnosis of this infection is needed to improve therapies, reduce transmission rates, and control the development of drug resistance. In 2011, the World Health Organization reported that TB infection causes 1.4 million deaths each year worldwide.

SUMMARY

The present disclosure provides, among other things, methods for screening a patient to determine if the patient is infected with a pathogen coupled with providing a treatment to the infected patient. In one aspect, the present disclosure provides apparatus and methods for collection and testing of samples. In a related aspect, the present disclosure also provides kits useful for performing disclosed methods and which kits may include various disclosed collection and testing apparatus.

In some embodiments, the present disclosure provides methods of detecting a pathogen that is present in a sample and correspondingly treating a patient infected with a pathogen. In some embodiments, methods of providing a blood sample include collecting a blood sample from a patient. In some embodiments, methods herein include a step of obtaining a collected sample of a patient or providing a blood sample from a patient.

In some embodiments, methods include collecting a blood sample from a patient by any means generally known in the art. In some embodiments, methods include collecting a blood sample from a patient infected with a pathogen. In some embodiments, methods include collecting a blood sample from a patient infected with a pathogen of a known origin or a pathogen of an unknown origin. In some embodiments, methods include collecting a blood sample from a healthy individual. In some embodiments, a healthy individual is free of or substantially free of a pathogen. As used herein, substantially refers to a qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. Substantially is therefore used herein to capture a potential lack of completeness inherent in many biological and chemical phenomena.

In some embodiments, a sample of blood is about 2 ml or less. In some embodiments, a sample of blood is about 5 ml or less.

In some embodiments, methods provided herein include a step of exposing a sample from a patient to one or more antigens of a pathogen. In some embodiments, a step of exposing includes steps of contacting, mixing, etc. a blood sample with one or more antigens of a pathogen. In some embodiments, a step of exposing includes steps of contacting, mixing, etc. a blood sample with a mixture or composition having one or more antigens of a pathogen.

In some embodiments, a step of exposing includes a step of contacting a sample with a mixture or composition having one or more antigens of a pathogen where the contacting step occurs in or on a titer plate, microtiter plate, microplate, microwell plate, multiwell, flat plate, or any plate with multiple wells used as small test tubes. In some embodiments, a step of exposing includes a step of contacting a sample with a mixture or composition having one or more antigens where the contacting step occurs in a capillary tube. In some embodiments, a capillary tube has an interior sidewall that is coated with one or more antigens for a pathogen. In some embodiments, contacting a sample with a capillary tube will cause drawing of a sample up and into a capillary tube. In some embodiments, inside walls of a capillary tube are coated with one or more antigens so that when a sample is drawn up and into a capillary tube, one or more antigens are exposed to, contact, come in contact with, or mix with such a sample.

In some embodiments, one or more antigens are in solution. In some embodiments, one or more antigens are lyophilized or freeze dried. In some embodiments, when freeze dried, one or more antigens are reconstituted prior to exposure to a sample. In some embodiments, when freeze dried, one or more antigens are reconstituted when exposed to a sample.

In some embodiments, when a pathogen is present in a sample and one or more antigens contact the sample, one or more antigens activate an immune response. In some embodiments, when a pathogen is present in a sample and one or more antigens contact the sample, one or more antigens enhance or increase an activated immune response. In some embodiments, an immune response generates an increase in immune cells. In some embodiments, an immune response generates an increase in T cells. In some embodiments, an immune response is local. In some embodiments, an immune response is systemic.

In some embodiments, provided methods include contacting a sample with a plurality of detectably-labeled antibodies. In some embodiments, contacting occurs, for example, in or on a plate, well, or tube as above explained. In some embodiments, a plurality of detectably-labeled antibodies that make contact with a sample are characterized in that they bind to or bind with cell activation markers. In some embodiments, a plurality of detectably-labeled antibodies that make contact with a sample are characterized in that they bind to or bind with a cell activation marker exposed on a surface of a cell. In some embodiments, a plurality of detectably-labeled antibodies that make contact with a sample are characterized in that they bind to or bind with a cell activation marker within a cell.

In some embodiments, a plurality of detectably-labeled antibodies is specific to a cell activation marker. In some embodiments, a plurality of detectably-labeled antibodies is specific to a cell activation marker present in or on an immune cell. In some embodiments, a plurality of detectably-labeled antibodies is specific to a cell activation marker present in or on an immune cell.

In some embodiments, a plurality of detectably-labeled antibodies have or include a detectable agent or moiety associated therewith. In some embodiments, a detectable agent or moiety refers to any element, molecule, functional group, compound, fragment or moiety that is detectable. In some embodiments, a detection entity is provided or utilized alone. In some embodiments, a detectable agent or moiety is provided and/or utilized in association with, or joined to another agent. In some embodiments, a detection entity is provided and/or utilized in association with another agent, for example, in a complex.

In some embodiments, for example, detection entities include, but are not limited to: various ligands; radionuclides, for example, $^3$H, $^{14}$C, $^{18}$F, $^{19}$F, $^{32}$P, $^{35}$S, $^{135}$I, $^{125}$I, $^{123}$I, $^{64}$Cu, $^{181}$Re, $^{111}$In, $^{90}$Y, $^{99m}$Tc, $^{177}$Lu, $^{89}$Zr etc.; fluorescent dyes; chemiluminescent agents, for example, acridinum esters, stabilized dioxetanes, bioluminescent agents; spectrally resolvable inorganic fluorescent semiconductors nanocrystals, for example, quantum dots; metal nanoparticles, for example, gold, silver, copper, platinum, etc.; nanoclusters; paramagnetic metal ions; enzymes, for example, horseradish peroxidase, beta-galactosidase, luciferase, alkaline phosphatase; colorimetric labels, for example, dyes, colloidal gold; biotin; dioxigenin; haptens; and proteins for which antisera or monoclonal antibodies are available.

In some embodiments, a plurality of detectably-labeled antibodies contact at least one activation marker. In some embodiments, a plurality of detectably-labeled antibodies bind with at least one activation marker. In some embodiments, a plurality of detectably-labeled antibodies bind with at least one activation marker to form a complex.

In some embodiments, provided methods include detecting a level of antibodies of a plurality of detectably-labeled antibodies bound to at least one activation marker of responding immune cells in a sample.

In some embodiments, methods of detection and quantification of signal generated by a complex formed will depend on a nature of an assay and of a detectable moiety, for example, a fluorescent moiety. In some embodiments, methods of detection and quantification of signal generated is by fluorescence microscopy or flow cytometry.

In some embodiments, protein expression in a biological sample is or may be determined using an immunoassay. In some embodiments, examples of such assays are time resolved fluorescence immunoassays (TRFIA), radioimmunoassays, enzyme immunoassays (e.g., ELISA), immunofluorescence immunoprecipitation, latex agglutination, hemagglutination, Western blot, and histochemical tests, which are conventional methods well-known in the art. In some embodiments, and as is be appreciated by a person of ordinary skill in the art, an immunoassay may be competitive or non-competitive.

In some embodiments, provided methods include detecting a level of one or more cytokines and/or chemokines in a sample. In some embodiments, cytokines and/or chemokines are characterized in that they are secretions from or by immune cells that respond to one or more antigens. In some embodiments, detecting a level of one or more cytokines and/or chemokines in a sample includes measuring a level of cytokines and/or chemokines.

In some embodiments, provided methods include detecting a level of one or more cytokines and/or chemokines in a sample includes determining whether a measured level of cytokines and/or chemokines in a sample is elevated relative to a reference level. In some embodiments, a reference level is determined from a sample that has not been exposed to a pathogen, is confirmed to lack or is substantially free of a pathogen.

In some embodiments, the present disclosure provides a general methodology of reacting a blood sample with one or more antigens followed by an assessment of immune cell (e.g. T cell) activation (e.g. via surface markers) and a cytokine and/or chemokine analysis. Specific immune cell surface markers, as well as particular cytokines (e.g. a particular level enhanced expression thereof), depend on a pathogen of interest and would create a T cell activation signature.

In some embodiments, provided methods include a step of determining whether a sample is infected with a pathogen include correlating a level antibodies of a plurality of detectably-labeled antibodies bound to at least one activation marker of responding immune cells and a level of one or more cytokines and/or chemokines of responding immune cells in a sample.

In some embodiments, provided methods include generating an immune cell activation signature from the detecting of the one or more labeled antibodies and the detecting of the one or more cytokines and/or chemokines.

In some embodiments, provided methods include treating a patient whose sample was determined to be infected by a pathogen. In some embodiments, if it is determined that responding immune cells of a patient, for example, T cells in a patient's blood were activated by one or more antigens of a pathogen, then the patient can be treated by administering a therapeutic or therapeutic regime for the infecting pathogen. In some embodiments, administering a therapeutic or therapeutic regime includes vaccinating a patient. In some embodiments, administering a therapeutic or therapeutic regime includes administering to the patient a regimen of antibiotics against a bacterial pathogen. In some embodiments, administering a therapeutic or therapeutic regime includes administering to the patient a regimen of antiviral medications against a viral pathogen. In some embodiments, administering a therapeutic or therapeutic regime includes administering to the patient a regimen of antifungal medications against a yeast or fungal pathogen. In some embodiments, administering a therapeutic or therapeutic regime includes administering to the patient a regimen of antiparasitic medications against a parasitic pathogen. In some embodiments, administering a therapeutic or therapeutic regime includes administering to the patient a regimen of anthelmintic medications against a pathogen that is a helminth.

In some embodiments, provided methods include a step of collecting a sample of blood from a patient into a capillary tube comprising sidewalls coated with one or more antigens of a pathogen, and allowing the blood to interact with one or more antigens for a period of time sufficient to activate T cells present in sample blood. In some embodiments, provided methods include, after allowing blood from a sample to interact with one or more antigens, contacting blood from a sample with a plurality of detectably-labeled antibodies that, respectively, specifically bind to T cell activation markers. In some embodiments, T cell activation markers include, but are not limited to CD4, CD25, CD26, CD27, CD28, CD31, CD39, CD44, CD45RA, CD45RO, CD62, CD62L, CD69, CD71, CD95, CD127, CD152, Forkhead Box P3 (FoxP3), L-selectin, C-C chemokine receptor type 7 (CCR7), Chemokine (C-X-C Motif) Receptor 3 (CXCR3), leukocyte function-associated antigen-1 (LFA-1), or Interleukin 2 Receptor beta (IL-2R$\beta$), and combinations thereof.

In some embodiments, after contacting a blood sample with a plurality of detectably-labeled antibodies, provided methods include a step of determining whether T cells from a patient's blood were activated by one or more antigens by detecting labeled antibodies bound to T cells. In some embodiments, after allowing blood from a sample to interact with one or more antigens, provided methods include determining whether T cells from a patient's blood were activated by one or more antigens by determining whether the level of one or more cytokines comprising Interleukin (IL) 2, IL-4, IL-6, IL-10, IL-12, Tumor Necrosis Factor alpha (TNF$\alpha$), Interferon gamma (IFN$\gamma$), or combinations thereof. In some embodiments, provided methods include comparing sample blood with blood from a healthy individual to determine if levels in sample blood are elevated over levels of IL-2, IL-4, IL-5, IL-6, IL-10, IL-12, TNF$\alpha$, IFN$\gamma$, or combinations thereof in a sample from a healthy subject.

In some embodiments, if it is determined that T cells in a patient blood were activate by one or more antigens, then provided methods further include treating a patient by vaccinating against a pathogen, by administering a regimen of antibiotics for a bacterial pathogen, by administering a regimen of antiviral medications for a viral pathogen, by administering a regimen of antifungal medications for a yeast or fungal pathogen, by administering a regimen of antiparasitic medications for a parasite, or by administering a regimen of anthelmintic medications if a helminth.

In some embodiments, a pathogen is a bacterium, and one or more antigens comprise one or more proteins or portion thereof expressed by a bacterium, where a bacterium is or includes *Mycobacterium tuberculosis, Mycobacterium ulcerans, Mycobacterium leprae, Mycobacterium avium, Mycobacterium intracellulare Chlamydia trachomatis, Treponema pertenue,* and *Vibrio cholera.*

In some embodiments, a pathogen is a virus, and one or more antigens comprise one or more proteins or portion thereof encoded by a virus, where a virus is or includes dengue virus, rabies virus, the chikungunya virus, the yellow fever virus, the human immunodeficiency virus (HIV) virus, and the Severe Acute Respiratory Syndrome (SARS) virus.

In some embodiments, a pathogen is a protozoa, and one or more antigens comprise one or more proteins or portion thereof expressed by a protozoa, where a protozoa is or includes *Plasmodium falciparum, Plasmodium vivax, Plasmodium ovale, Plasmodium malariae, Trypanosoma cruzi, Trypanosoma brucei, Leishmania donovani, Leishmania infantum,* and *Leishmania chagasi.*

In some embodiments, a pathogen s a helminth, and one or more antigens comprise one or more proteins or portion thereof expressed by a helminth, where a helminth is or includes *Taenia solium, Dracunculus medinensis, Echinococcus multilocularis, Clonorchis sinensis, Wuchereria bancrofti, Brugia malayi, Brugia timori, Onchocerca volvulus, Schistosomiasis cercariae, Ascaris lumbricoides, Trichuris trichiura, Ancylostoma duodenale,* and *Necator americanus.*

In some embodiments, provided methods include T cell activation markers, including C-C chemokine receptor type 3 (CCR3), C-C chemokine receptor type 4 (CCR4), C-C chemokine receptor type 5 (CCR5), C-C chemokine receptor type 8 (CCR8), Chemokine (C-X-C Motif) Receptor 5 (CXCR5), or IFN$\gamma$ Induced Protein 10 (IP-10) or combinations thereof.

In some embodiments, provided methods include a plurality of detectably-labeled antibodies, including those that specifically bind to CD4, CD25, CD44, CD62, CD69, and CD71.

In some embodiments, provided methods include activating T cells including for example one or more of CD4+ $T_{Reg}$ cells, $T_{CM}$ cells, $T_{EM}$, $T_{EMRA}$, or $T_{SCM}$ cells.

In some embodiments, provided methods include activating CD4+ $T_{Reg}$ cells. In some embodiments, provided methods further include a step of contacting a sample having activated CD4+ $T_{Reg}$ cells with a plurality of detectably-labeled antibodies that include a plurality of detectably-labeled antibodies that specifically bind to CD4, CD25, CD26, CD31, CD39, CD127, CD152, and FoxP3.

In some embodiments, provided methods include activating $T_{CM}$ cells. In some embodiments, provided methods further include a step of contacting a sample having activated $T_{CM}$ cells with a plurality of detectably-labeled antibodies that include a plurality of detectably-labeled antibodies that specifically bind to L-selectin and CCR7.

In some embodiments, provided methods include activating $T_{SCM}$ cells. In some embodiments, provided methods further include a step of contacting a sample having activated $T_{SCM}$ cells with a plurality of detectably-labeled antibodies that include a plurality of detectably-labeled antibodies that specifically bind to CD27, CD28, CD45R0, CD45RA, CD62L, CD95, CCR7, CXCR3, LFA-1, and IL-2R$\beta$.

In some embodiments, provided methods include activating $T_{CM}$ or $T_{EM}$ cells. In some embodiments, provided methods further include a step of contacting a sample having activated $T_{CM}$ or $T_{EM}$ cells with a plurality of detectably-labeled antibodies that include a plurality of detectably-labeled antibodies that specifically bind to CD45RO and CD45RA.

In some embodiments, methods provided herein include detecting one or more cytokines. In some embodiments, methods provided herein include detecting IL-1, IL-3, IL-8, IL-13, IL-23, IL-27, or combinations thereof.

In some embodiments, methods provided herein include determining whether T cells in a patient blood were activated by one or more antigens. In some embodiments, determining whether T cells in a patient blood were activated by one or more antigens includes detecting labeled antibodies bound to T cells and determining a level of one or more cytokines including IL-1, IL-2, IL-3, IL-5, IL-6, IL-8, IL-10, IL-12, IL-13, IL-23, IL-27, TNF$\alpha$, IFN$\gamma$, or combinations thereof is present in a blood sample of a patient. In some embodiments, determining whether T cells in a patient blood were activated by one or more antigens includes detecting labeled antibodies bound to T cells and determining whether a level of one or more cytokines including IL-1, IL-2, IL-3, IL-4, IL-5, IL-6, IL-8, IL-10, IL-12, IL-13, IL-23, IL-27, TNF$\alpha$, IFN$\gamma$, or combinations thereof is elevated over a level of IL-1, IL-2, IL-3, IL-4, IL-5, IL-6, IL-8, IL-12, IL-13, IL-23, IL-27, TNF$\alpha$, IFN$\gamma$, or combinations thereof in the blood of a healthy subject.

In some embodiments, methods provided herein further include determining whether T cells in a patient blood were activated by one or more antigens. In some embodiments, determining whether T cells in a patient blood were activated by one or more antigens includes detecting labeled antibodies bound to T cells and determining whether a level of one or more cytokines including IL-2, IL-6, and TNFα, or combinations thereof is present in a blood sample of a patient. In some embodiments, determining whether T cells in a patient blood were activated by one or more antigens includes detecting labeled antibodies bound to T cells and determining whether a level of one or more cytokines including IL-2, IL-6, and TNFα, or combinations thereof is elevated over a level of IL-2, IL-6, and TNFα, or combinations thereof in the blood of a healthy subject.

In some embodiments, methods as provided herein include a period of time sufficient to activate T cells in a blood sample. In some embodiments, a period of time is from about 4 hours to about 24 hours. In some embodiments, a period of time is from about 1 hours to about 48 hours.

In some embodiments, methods as provided herein include a detecting step performed using a flow cytometer and/or flow cytometry techniques known to a person of ordinary skill in the art.

In some embodiments, methods as provided herein include repeating at least one of the disclosed steps after a time interval. In some embodiments, steps are repeated to confirm results. In some embodiments, steps are repeated by varying combinations of one or more antigen and plurality of detectably labeled antibodies. In some embodiments, steps are repeated by varying combinations of one or more antigen and plurality of detectably labeled antibodies to detect varying pathogens and administer corresponding treatment. In some embodiments, a time interval is at least about three months, at least about six months, at least about one year, at least about two years, or more.

In some embodiments, the present disclosure provides kits for determining a presence of a pathogen in a subject. In some embodiments, kits include one or more antigens of the pathogen and a plurality of capillary tubes having the one or more antigens coated on an interior wall.

BRIEF DESCRIPTION OF THE DRAWING

The foregoing and other objects, aspects, features, and advantages of the present disclosure will become more apparent and better understood by referring to the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following Figs..

DEFINITIONS

Figure 1A:
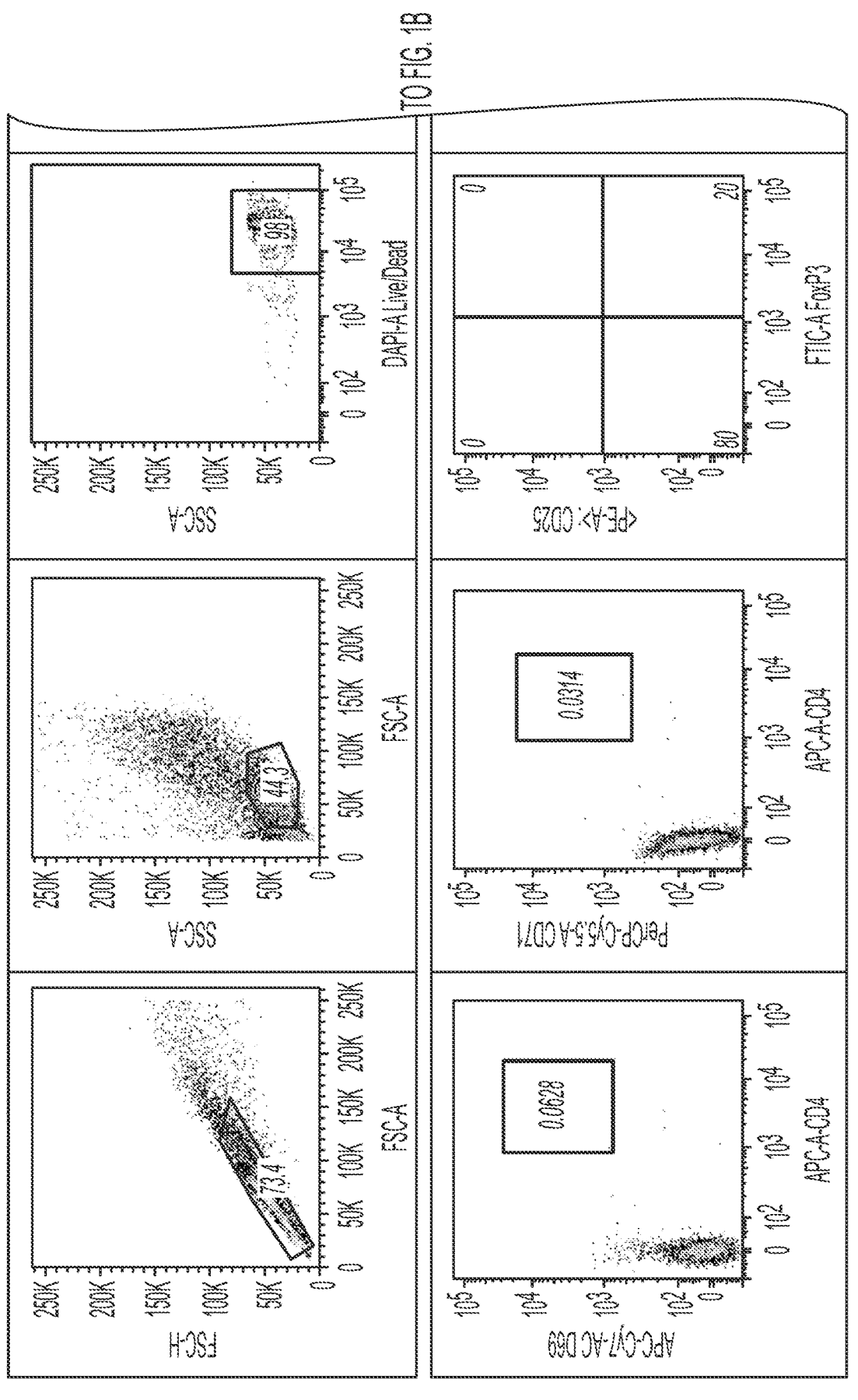
FIGS. 1A and 1B show flow cytometry plots showing staining for activation markers on unstimulated T cells.

Various terms relating to aspects of the present disclosure are used throughout the specification and claims. Such terms are to be given their ordinary meaning in the art, unless otherwise indicated. In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or," In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The terms subject or patient are used interchangeably. A subject may be any animal, including mammals such as companion animals, laboratory animals, and non-human primates. Human beings are preferred.

DETAILED DESCRIPTION

The present disclosure provides methods and kits for activating, detecting, and enumerating protein activation markers indicative of cellular events in a biological sample. Specifically, the present disclosure provides, for example, methods and kits for activating an immune response, detecting such a response, including for example, antibody panels coupled with optimized fluorescent molecules. Detection of a cell mediated immune response in response to the presence of specific antigens from infective agents (bacteria, protozoa, viruses, helminth, prions) can be utilized in vitro to diagnose multiple infections within individuals.

The present disclosure encompasses a recognition that provided kits and methods can be utilized as part of a platform for the diagnosis of specific infectious diseases, many of which are presented during early infection with similar clinical symptoms, for example, fever or rash; for rapid detection of infective agents in small volumes of capillary blood; to distinguish isotypes or serotypes of infective agent, for example Dengue Fever Viruses (DENY serotypes, Malaria causing *Plasmodium* parasites); to identify patients with co- or multiple infections caused by infection with more than one infective agent; and/or to distinguish between active and latent infection, such in the example of Tuberculosis infection; patients will latent infection carry an infective agent and their condition can transition to active infection, example during periods of immune-compromise.

The present disclosure further encompasses a recognition that flow cytometry allows scientists to examine individual cells, such as white blood cells. Cells can be labelled using antibodies conjugated with fluorescent molecules. Each antibody species bind with a specific protein that may be present on a surface or in a cytoplasm of cells. Flow cytometry measures a presence or absence of a fluorescently-labelled antibody on or in cells, indicating a presence or absence of a target cellular protein. Flow cytometry operates by passing cells in a uniform stream through a laser beam. Emission spectra from fluorescently labelled antibodies is detected by photomultiplier tube detectors.

The current standards in diagnostic assays are the tuberculin skin test or Mantoux test and a recently-developed T-cell based interferon gamma release assay, however neither test can reliably distinguish between vaccination versus active TB or latent TB infection. Although more sensitive than the skin test, the interferon gamma release assay provides limited usefulness in patients with concomitant infections such as HIV. The skin test is unable to distinguish between active and latent infection. Neither assay provides information on drug-resistance phenotypes. In addition, there are various conditions such as oncologic disease, parasitic and HIV infection, diabetes, renal failure and other immuno-compromising conditions that produce intermediate or false negative results using the interferon gamma release assay.

Alternative methods for clinical diagnosis include the culturing of bacterial cultures from sputum. This method requires technicians to handle highly infective body fluid, and is both time and labor intensive, requiring up to 6 weeks to complete before an accurate diagnosis can be made, and its use is associated with an increased incidence of reoccurrence of infection. This type of test is expensive, and has a high level of inaccuracy caused by cross contamination or mishandling and, therefore, does not represent a feasible method of diagnosis in most parts of the globe.

More recently, PCR-based assays have been developed for the detection of the TB bacterium. These tests are relatively complex, requiring on site sample processing of sputum. Limitations of such assays include the inability to distinguish between active and latent infection or provide any information on the immune response exhibited by the individual patient; rather, the assays are qualitative in nature. In addition, the cost of PCR assays makes them feasible primarily as a second line of testing. Even the most advanced PCR test currently available produces an unacceptably high (~10%) rate of false positive results.

The present disclosure and embodiments of the present disclosure solve important problems with making cost-effective and accurate diagnoses for enhancing infection control and quelling the spread of communicable diseases.

In some embodiments, the present disclosure relates to the understanding that particular T cell subsets respond to different pathological infections. While not wishing to be bound to a particular theory, it is believed that particular T cell activation markers may coordinate with different pathogens. Moreover, it is believed that particular cytokine expression profiles coordinate with T cell activation markers.

In some embodiments, combinations of T cell activation markers and cytokine expression profiles surprisingly evidence pathogenic infections with a relatively high degree of confidence. In some embodiments, T cell activation profiles (i.e. activation markers and cytokine expression) may be used as part of a diagnostic modality suitable for rapid field diagnoses of pathogenic infections, particularly where time-consuming, complex, expensive, invasive, and/or multi-platform diagnostic testing is not practical or even feasible. Accordingly, in some embodiments, the present disclosure features methods for screening a patient to determine if a patient is infected with a pathogen. In some embodiments, screening methods devise patient biological data and comprise part of the diagnostic process.

In some embodiments, methods include interacting a blood sample obtained from a patient with one or more, antigens of a pathogen in order to activate immune cells. In some embodiments, immune cells are or include T cells present in a sample of blood. In some embodiments, methods include labeling immune cells by contacting a blood sample with detectably labeled antibodies that specifically hind to immune cells activation markers. In some embodiments, methods include determining whether immune cells present in a sample blood were activated by one or more antigens by detecting labeled antibodies bound to such immune cell activation markers. In some embodiments, methods include measuring a level of cytokines and/or chemokines in a sample of a patient. In some embodiments, methods include measuring a level of cytokines and/or chemokines in a blood sample of a patient. In some embodiments, methods include determining whether a measured level of cytokines and/or chemokines in a sample are elevated to a level that indicates that immune cells in blood are activated. In some embodiments, methods include determining whether a measured level of cytokines and/or chemokines in a sample are elevated to a level corresponding to that of a sample from a healthy individual. If immune cells are evidenced as activated, a patient may be administered therapeutic agents as appropriate to treat an identified pathogen.

Pathogens

In some embodiments, methods provided herein may be useful to detect, diagnose, or screen infection with any pathogen. In some embodiments, pathogens may be unicellular or multicellular. In some embodiments, pathogens may be prokaryotic or eukaryotic. In some embodiments, pathogens may include a virus or prion. In some embodiments, pathogens may include a bacteria, a protozoa, a yeast or fungus, or a helminth.

In some embodiments, methods provided herein may be useful to detect, diagnose, or screen disease, for example, tropical infections, including neglected tropical diseases.

In some embodiments, pathogens are or include bacterium. In some embodiments, bacterium are or include a causative agent of tuberculosis, *Mycobacterium tuberculosis*, a causative agent of a Buruli ulcer, *Mycobacterium ulcerans*, a causative agent of leprosy, *Mycobacterium leprae*, a causative agent of the *Mycobacterium Avium* Complex (MAC), *Mycobacterium avium* or *Mycobacterium intracellulare*, a causative agent of trachoma, *Chlamydia trachomatis*, a causative agent of Yaws, *Treponema pertenue* or a causative agent of cholera, *Vibrio cholera.*

In some embodiments, pathogens are or include a virus. In some embodiments, a virus is or include a causative agent of dengue fever, the dengue virus, a causative agent of rabies, the rabies virus, a causative agent of chikungunya, the chikungunya virus, a causative agent of yellow fever, the yellow fever virus, a causative agent of Severe Acute Respiratory Syndrome (SARS), the SARS virus, or a causative agent of the Acquired Immune Deficiency Syndrome (AIDS), the human immunodeficiency virus (HIV).

In some embodiments, pathogens are or include a protozoa. In some embodiments, a protozoa is or includes a causative agent of malaria, *Plasmodium falciparum*, *Plasmodium vivax*, *Plasmodium ovale*, or *Plasmodium malariae*, may include a causative agent of African trypanosomiasis (sleeping sickness), *Trypanosoma cruzi* or *Trypanosoma brucei*, or may include a causative agent of leishmaniases, *Leishmania donovani*, *Leishmania infantum* or *Leishmania chagasi.*

In some embodiments, pathogens are or include a helminth. In some embodiments, a helminth is or includes a causative agent of cysticercosis/taeniasis, *Taenia solium*, a causative agent of dracunculiasis (guinea-worm disease), *Dracunculus medinensis*, a causative agent of Echinococcosis, *Echinococcus multilocularis*, a causative agent of foodborne trematodiases, *Clonorchis sinensis*, a causative agent of lymphatic filariasis, *Wuchereria bancrofti*, *Brugia malayi*, or *Brugia timori*, a causative agent of Onchcerciasis river blindness), *Onchocerca volvulus*, a causative agent of schistosomiasis, *Schistosomiasis cercariae*, or a causative agent of soil-transmitted helminthiases, *Ascaris lumbricoides*, *Trichuris trichiura*, *Ancylostoma duodenale*, or *Necator americanus.*

Antigens

In some embodiments, one or more antigens may comprise any antigens that activate immune cells in blood. In some embodiments, one or more antigens may, for example, be antigens exposed on an exterior surface of a cell. In some embodiments, one or more antigens may, for example, be antigens exposed to cytoplasm of a cell. In some embodiments, antigens are or include viral coat antigens, bacterial or viral capsule antigens, or other suitable antigens. In some embodiments, one or more antigens are or include polypeptides, or proteins, or any portion or combination thereof. In some embodiments, one or more antigens may include glycoproteins, nucleic acids, lipids, or other suitable antigens capable of activating T cells as a signal of an invading etiologic agent.

In some embodiments, an antigen's presence or level correlates with elevated level or activity, as compared with that observed absent the antigen. In some embodiments, an antigen's presence or level correlates with a target level of activity that is comparable to or greater than a particular reference level or activity, that is observed under an appropriate reference condition.

Sample

In some embodiments, methods include a step of obtaining a fluid sample from a patient. In some embodiments, a fluid sample is any bodily fluid. In some embodiments, a fluid sample is a blood sample.

In some embodiments, methods include a step of obtaining a blood sample from a patient. In some embodiments, a blood sample may be collected by any means known in the art. In some embodiments, a volume of a blood sample is about 0.5 mL to about 5 mL. In some embodiments, a volume of a blood sample is less than about 5 mL, less than about 4 mL, less than about 3 mL, less than about 2.5 mL, less than about 2 mL, less than about 1.5 mL, less than about 1 mL, less than about 0.5 mL.

In some embodiments, a blood sample is collected in one or more small volume capillary tubes. In some embodiments, capillary tubes may hold a volume of, for example, about 0.5 mL to about 3 mL. In some embodiments, a capillary tube may hold a volume, for example, including about 0.5 mL, about 1 mL, about 1.5 mL, about 2 mL, about 2.5 mL, about 3 mL, about 3.5 mL, about 4 mL, about 4.5 mL, or about 5 mL, or more. In some embodiments, capillary tubes may be fabricated from or include plastic, polymer, rubber, or glass.

In some embodiments, interior side walls of capillary tubes are coated with one or more antigens of a pathogen. In some embodiments, interior side walls of capillary tubes are coated with only one particular pathogen's antigens. In some embodiments, interior side walls of each capillary tube are coated with only one particular pathogen's antigens.

In some embodiments, one or more antigens may be coated onto interior side walls of a capillary tube according to any suitable methodology. In some embodiments, coating one or more antigens onto interior side walls of a capillary tube includes filling a capillary tube with a composition having one or more antigens present in a liquid carrier. In some embodiments, coating one or more antigens onto interior side walls of a capillary tube further includes drying or lyophilizing a filled tube. In some embodiments, drying or lyophilizing a filled tube removes a liquid carrier and leaves behind antigen. In some embodiments, dried or lyophilized antigen on an interior side wall of a capillary tube is resuspended when it is brought into contact with a sample, such as a blood sample. In some embodiments, capillary tubes include an anti-coagulant agent to keep a sample, such as a blood sample, present or collected in a capillary tube in its liquid form. In some embodiments, capillary tubes include an anti-coagulant agent to keep a blood sample, present or collected in a capillary tube in its liquid form during a period in which immune cells may interact with antigen.

In some embodiments, antigen freely interacts with cells present in a sample.

In some embodiments, one or more antigens and blood cells interact for a period of time sufficient to allow immune cells, such as T cells present in a blood sample to be activated. In some embodiments, a period of time may be or include from about 1 hour to about 48 hours. In some embodiments, a period of time may be or include from about 4 hours to about 24 hours.

In some embodiments, one or more antigens and blood cells interact in an incubator. In some embodiments, an incubator is controlled for temperature, humidity, and other environmental conditions. In some embodiments, one or more antigens and blood cells interact at body temperature, or about 37 degrees Celsius.

Immune Cells (e.g. T Cells)

In some embodiments, when a blood sample is exposed to one or more antigens, such exposure initiates or enhances an immune response. In some embodiments, an immune response includes responding immune cells.

In some embodiments, methods as provided herein may be used to measure activation of immune cells that participate in a cellular immune response. In some embodiments, methods as provided herein may be used to measure activation of T cells that participate in a cellular immune response. In some embodiments, methods do not measure activation of helper T cells (e.g., CD4+ $T_H$ cells). In some embodiments, methods do not measure a humoral immune response.

In some embodiments, T cells may include one or more of regulatory T cells such as CD4+ TReg cells, central memory T cells (TCM cells), stem memory T cells (TSCM cells), effector memory T cells (TEM cells), or effector memory RAT cells (TEMRA cells). In some embodiments, methods as provided herein include selecting detectably-labeled antibodies and as such may include choosing to assess one or more of sub-populations of T cells.

Activation Markers

In some embodiments, detectably-labeled antibodies probe activation markers present on or associated with immune cells, e.g. T cells. In some embodiments, probed activation markers may include one or more of CD4, CD25, CD26, CD27, CD28, CD31, CD39, CD44, CD45RA, CD45RO, CD62, CD62L, CD69, CD71, CD95, CD127, CD152, Forkhead Box P3 (FoxP3), L-selectin, C-C chemokine receptor type 7 (CCR7), Chemokine (C-X-C Motif) Receptor 3 (CXCR3), leukocyte function-associated antigen-1 (LFA-1), Interleukin 2 Receptor beta (IL-2Rβ), C-C chemokine receptor type 3 (CCR3), C-C chemokine receptor type 4 (CCR4), C-C chemokine receptor type 5 (CCR5), C-C chemokine receptor type 8 (CCR8), Chemokine (C-X-C Motif) Receptor 5 (CXCR5), or IFNγ Induced Protein 10 (IP-10). In some embodiments, any combination of activation markers may be probed with detectably-labeled antibodies. In some embodiments, combinations of activation markers are or include CD4, CD25, CD69, and CD71. In some embodiments, combinations of activation markers are or include CD25, CD44, CD62, and CD69. In some embodiments, T cells include CD4+ TReg cells and combinations of activation markers are or include CD4, CD25, CD26, CD31, CD39, CD127, CD152, and FoxP3. In some embodiments, T cells include TCM cells and combinations of activation markers are or include L-selectin and CCR7. In some embodiments, T cells TSCM cells and combinations of activation markers are or include CD27, CD28, CD45R0, CD45RA, CD62L, CD95, CCR7, CXCR3, LFA-1, and IL-2Rβ. In some embodiments, TCM and TEM cells exhibit enhanced expression of CD45RO and simultaneous diminished expression of CD45RA.

Detection

In some embodiments, activation of an immune cell, for example, a T cell occurs with pathogen exposure. In some embodiments, methods of detecting, determining, and/or identifying a pathogen as provided herein are surprising reliable and accurate. In some embodiments, combining methods of detecting, determining, and/or identifying surprisingly produces higher accuracy and reliability than such methods alone.

In some embodiments, methods provided herein include a screening methodology that devises patient biological data. In some embodiments, a screening methodology includes determining whether a patient carries one or more pathogens or is infected with one or more pathogens, thereby forming a screening profile. In some embodiments, a patient biometric profile (including but not exclusively fingerprint, iris scan, retinal scan), including such a profile and these biological data may all be linked together for medical record keeping.

Antibody Detection

In some embodiments, methods as provided herein include providing a detectable label or detectably labeled antibodies. In some embodiments, a label is or includes a fluorescent label. In some embodiments, antibodies do not cross-react with multiple T cell activation markers. In some embodiments, a plurality of antibodies is used. In some embodiments, each member of a plurality of antibodies specifically binds to a particular T cell activation marker of interest.

In some embodiments, methods provided herein include contacting detectably-labeled antibodies with a blood sample. In some embodiments, after contacting detectably-labeled antibodies with a blood sample a period of time elapses. In some embodiments, a period of time allows interaction of detectably-labeled antibodies with activated immune cells in the sample. In some embodiments, a period of time allows detectably-labeled antibodies to bind to a corresponding antigen present on or in activated immune cells, T cells. In some embodiments, at least a portion of unbound antibodies may be washed from cells or sample. In some embodiments, red blood cells present in a blood sample may be lysed or otherwise removed from a sample anytime prior to analysis.

In some embodiments, methods provided herein include detecting one or more labeled antibodies bound on immune cells. In some embodiments, methods provided herein include detecting one or more labels on immune cell bound antibodies. In some embodiments, methods provided herein include detecting one or more labels on T cell-bound antibodies. In some embodiments, detecting T cell activation is determined by detecting one or more labels on T cell-bound antibodies.

In some embodiments, methods provided herein include methods of detecting such labels, for example, fluorescence microscopy or flow cytometry may be used for detecting. In some embodiments, detecting labels may permit a determination of whether an immune cell was activated. In some embodiments, detecting labels may permit a determination of whether an immune cell was activated in response to antigen exposure.

In some embodiments, methods provided herein include comparing activated T cells relative to unactivated or unstimulated T cells. In some embodiments, methods include determining T cell activation, for example, by establishing a fluorescent intensity of activation markers on activated T cells. In some embodiments, methods include determining unactivated or unstimulated T cells, for example, by running appropriate controls in parallel.

Cytokine Detection

In some embodiments, methods provided herein include determining immune cell activation. In some embodiments, methods provided herein further include determining a level of one or more cytokines. In some embodiments, methods provided herein further include determining a level of one or more of Interleukin IL-1, IL-2, IL-3, IL-4, IL-5, IL-6, IL-8, IL-10, IL-12, IL-13, IL-23, IL-27, Tumor Necrosis Factor alpha (TNFα), Interferon gamma (IFNγ), or combinations thereof in antigen-reacted blood of a patient. In some embodiments, elevated levels of one or more of cytokines may serve as an indicator of T cell activation. In some embodiments, methods provided herein include determining whether levels of one or more cytokines is elevated over levels of same cytokines in unstimulated blood, i.e. blood from a subject that is healthy or at least not infected with a queried pathogen, or that has otherwise not been reacted with pathogen antigens present within a capillary tube. In some embodiments, an elevated level may be about 2 time to about 3 times the level of the cytokine expected or observed from a healthy or non-infected individual.

Determination

In some embodiments, it is particularly useful, for example, where even with respect to a particular class of pathogens (e.g., bacteria, virus, yeast, parasite, or helminth), one particular agent may be effective against one particular type of pathogen, but not another type of pathogen (e.g., an antibiotic may be effective against one bacteria type, but not another bacteria type). Accordingly, in some embodiments, accurate diagnoses made according to screening methodologies described or exemplified herein may be used to direct the most appropriate therapeutic agent to use in the treatment regimen. This stands in stark contrast to non-specific or broad spectrum approaches currently in use, which may be ineffective when not tailored to the actual causative agent of the patient's infection.

In some embodiments, an underlying diagnostic modality provides an accurate assessment of an underlying infection. In some embodiments, pathogenic infections mimic each other in terms of symptoms and manifestations on or within the patient. In some embodiments, absent a more definitive assessment of a particular infectious agent, valuable time and effort may be wasted by providing a patient with an incorrect therapeutic agent, or an incorrect dose of a therapeutic agent.

In some embodiments, when used in combination a T cell activation marker analysis and cytokine analysis together provide an indication that a sample of T cells from a patient were activated by one or more pathogen antigens. In some embodiments, methods as provided herein when a combined indication has a surprisingly high rate of diagnosis when compared with either activation indicator alone.

In many cases, a particular patient may have multiple infections at one time. In some embodiments, screening methods may be repeated using any number of antigen-containing capillary tubes, with each tube containing antigens from a different pathogen. In some embodiments, a general screening and treatment methodology as disclosed, includes assessing a reaction between blood and antigens with a determination of T cell activation via assessing T cell surface markers in combination with a cytokine and/or chemokine analysis. In some embodiments, particular T cell surface markers being tested may vary, as well as particular cytokines, depending on a particular pathogen of interest. In some embodiments, it is believed that particular pathogens coordinate with particular T cell types, T cell activation markers, and cytokine expression such that particular pathogens create a T cell activation signature. In some embodiments, a T cell activation signature comprises a particular subset of T cell activation markers, and a particular subset of cytokines, and in some cases, a particular level of enhanced expression of such cytokines.

In some embodiments, methods as provided herein may be repeated over time. In some embodiments, for example, methods may be repeated following a treatment regimen, to determine if a treatment has cleared an infection. In some embodiments, methods as provided herein may also be repeated based on encountering an individual or group in a different geographic location. In some embodiments, a period of time between repeats is not critical, and can vary according to needs of individual patients, needs of particular healthcare providers. In some embodiments, methods are repeated after a period of about 2 months, after a period of about 3 months, after a period of about 4 months, after a period of about 6 months, after a period of about 9 months, after a period of about a year, after a period of about a year and a half, after a period of about 2 years, after a period of about 3 years, after a period of about 4 years, after a period of about 5 years, or longer than about 5 years.

Treatment

In some embodiments, methods include administering a treatment when combined determining factors indicate an infection is present in a sample.

In some embodiments, treatments may vary, for example, according to a particular pathogen or a class of pathogen. In some embodiments, for example, if a pathogen is a bacterium, methods may include administering to a regimen of antibiotics to an infected patient. In some embodiments, for example, if a pathogen is a virus, methods may include administering a regimen of antiviral medication to an infected patient. In some embodiments, for example, if a pathogen is a yeast or fungus, methods may include administering a regimen of antifungal medications to an infected patient. In some embodiments, for example, if a pathogen is a parasite, methods may include administering a regimen of antiparasitic medications to a patient. In some embodiments, for example, if the pathogen is a helminth, methods may include administering a regimen of anthelmintic medications to a patient. In some embodiments, treating or administering a course of treatment may include vaccinating a patient against a pathogen.

Kits

In some embodiments, the present disclosure further provides kits for determining and detecting pathogens as described herein. In some embodiments, a kit is useful for determining whether a subject is infected with a pathogen. In some embodiments, a kit comprises agents for determining a presence, level and/or location of one or more particular pathogens.

In some embodiments, kits comprising various reagents and materials useful for carrying out inventive methods according to the present disclosure. In some embodiments, diagnosis and treatment procedures described herein may be performed by diagnostic laboratories experimental laboratories, or practitioners. In some embodiments, the present disclosure provides kits which can be used in these different settings.

In some embodiments, for example, materials and reagents for determining whether a subject is infected with a pathogen, diagnosing pathogens, identifying pathogens, distinguishing pathogens, discerning active and latent infection, characterizing severity of infection, monitoring exposure, and/or monitoring treatment response in a subject according to the inventive methods may be assembled together in a kit.

In some embodiments, an inventive kit comprises at least one or more antigens to active an immune cell (e.g. T cell)

response. In some embodiments, each kit may include an antigen reagent or composition which renders the procedure specific to a pathogen. Thus, for detecting/quantifying a protein marker (or an analog or fragment thereof), the reagent that specifically detects expression levels of the protein may be an antibody that specifically binds to the protein marker (or analog or fragment thereof).

In some embodiments, kits or other articles of manufacture according to the disclosure may include capillary tubes. In some embodiments, kits or other articles of manufacture according to the disclosure may include capillary tubes having at least one antigen coated on interior walls thereof. In some embodiments, kits or other articles of manufacture according to the disclosure may include a plurality of capillary tubes for a same specific pathogen, antibody, and/or activation marker. In some embodiments, kits or other articles of manufacture according to the disclosure may include a plurality of capillary tubes for different pathogens, antibodies, and/or activation markers.

In some embodiments, kits or other articles of manufacture according to the disclosure may include one or more containers to hold various reagents. In some embodiments, kits having suitable containers include, for example, bottles, vials, syringes (e.g., pre-filled syringes), ampules. In some embodiments, containers may be formed from a variety of materials such as glass or plastic.

In some embodiments, kits of the present disclosure may include suitable reference levels or reference samples for determining reference levels as described herein. In some embodiments, kits of the present disclosure may include instructions for use according to one or more methods of the present disclosure and may comprise instructions for processing a biological sample obtained from a subject and/or for performing a test, instructions for interpreting results as well as a notice in the form prescribed by a governmental agency (e.g., FDA) regulating the manufacture, use or sale of pharmaceuticals or biological products.

EXEMPLIFICATION

The following examples illustrate some embodiments and aspects of the present disclosure. It will be apparent to those skilled in the relevant art that various modifications, additions, substitutions, and the like can be performed without altering the spirit or scope of the disclosure, and such modifications and variations are encompassed within the scope of the disclosure as defined in the claims, which follow. The present disclosure will be more fully understood by reference to these examples. The following examples do not in any way limit the present disclosure or the claimed disclosures and they should not be construed as limiting the scope.

Example 1

The present example describes T cell activation detected by flow cytometry.

Human whole blood was obtained and diluted 1:5 in RPMI media, then stimulated with either 0, 20, 40, 60, 80, 100 μg/mL (of blood) of phytohemagglutinin (PHA) for about 20 hours at 37° C. and 5% $CO_2$. In parallel, blood samples were treated with a buffer (no PHA) as a stimulation control. Following the stimulation period, blood samples were stained with fluorescently-labeled antibodies to T cell markers, including CD4, CD25, CD69, and CD71.

Fluorescently-labeled (FITC, APC, PE, PerCP-Cy5, APC-Cy7) antibodies were mixed with 100 μL of PHA-stimulated blood samples or with unstimulated blood control samples in parallel, and each of the samples were then incubated, protected from light, for a minimum of 30 minutes. Following incubation with the labeled antibodies, the samples were washed with BSA Stain Buffer. In parallel, samples were separately incubated with isotype control antibodies.

Following washing, red blood cells were lysed with 1 mL of Ix Pharm Lyse™ by incubation with this reagent for 15 minutes. Samples were next centrifuged, then washed again with BSA Stain Buffer. All samples were fixed and permeabilized with eBiosciences Fix and Perm solutions according to the manufacturer's instructions.

FoxP3 was added to the fixed/permeabilized samples, and the samples were then incubated for a minimum of 30 minutes. Samples were then again washed with BSA Stain Buffer. Next, 1 μL of Violet Live/Dead was added to the samples and incubated, protected from light, for a minimum of 15 minutes.

Samples and controls were then run through a FACSAria III flow cytometer. The machine was calibrated, and compensation was performed according to standard requirements and procedures. Cells were suspended at a density of 1,000,000 cells per mL in a tube, and run through the flow cytometer for analysis. One hundred thousand events were collected per analysis.

T cells were identified by their forward (FSC) and side (SSC) scatter profiles, and gated accordingly. T cells were then further analyzed according to the T cell marker profiles (Fox3, CD4, CD25, cD69, and CD71). Representative flow cytometry plots showing these T cell marker analyses are shown in FIGS. 7 through 10.

Figure 1B:
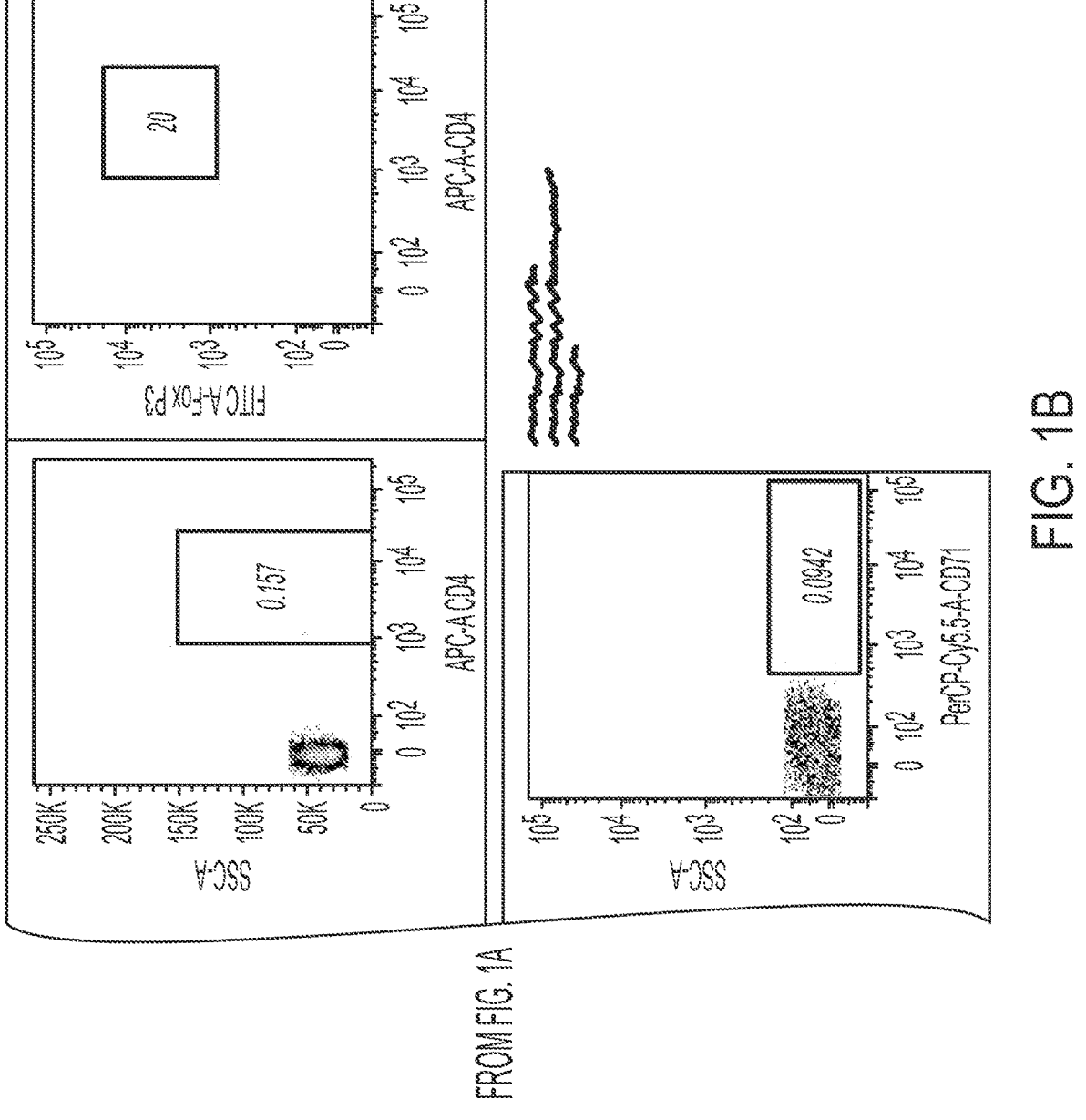
Figure 2A:
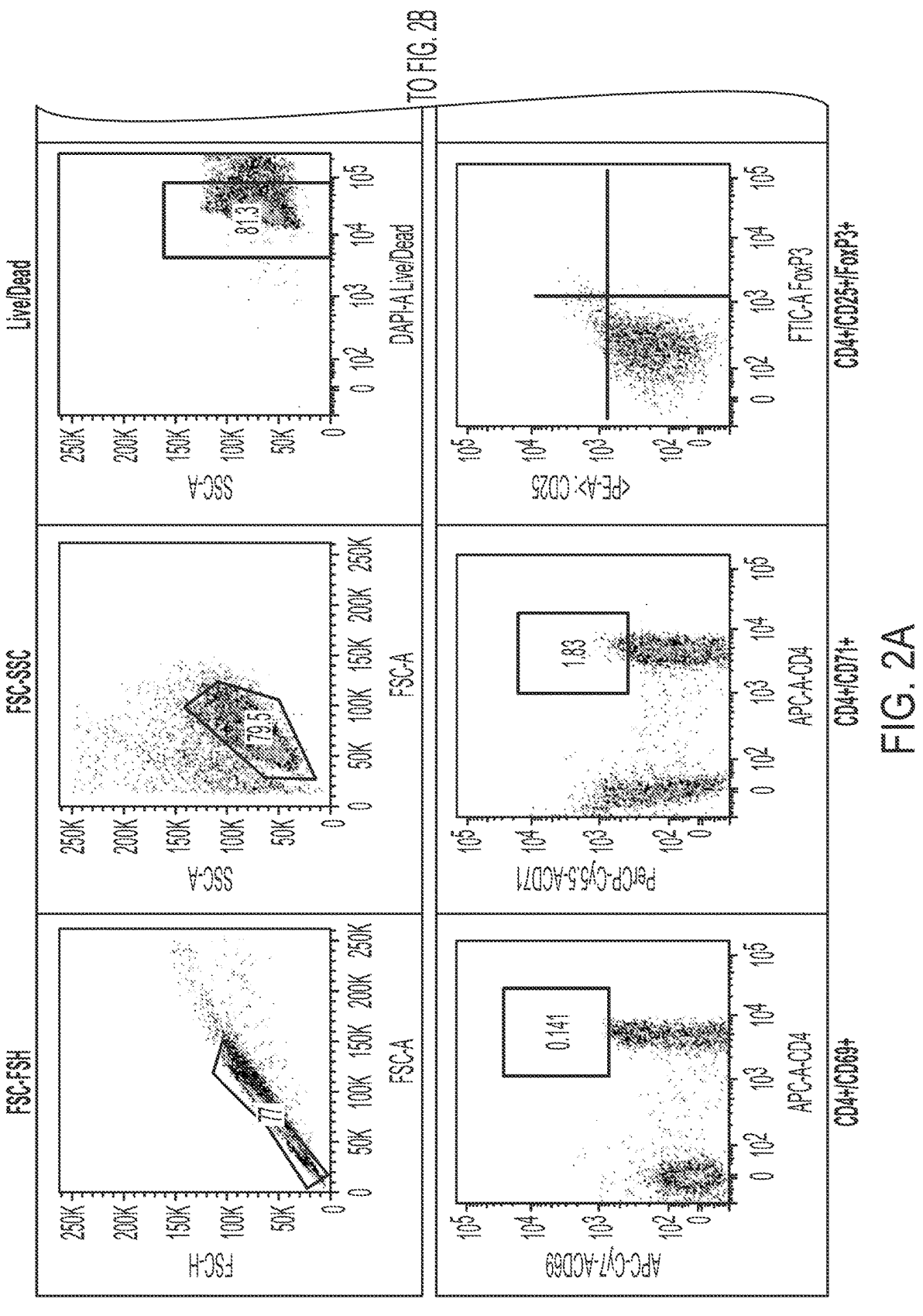
FIGS. 2A and 2B show flow cytometry plots showing staining for activation markers on T cells stimulated with 10 μg/mL of Phytohemagglutinin (PHA), a non-specific activator of the cell mediated immune response.
Figure 2B:
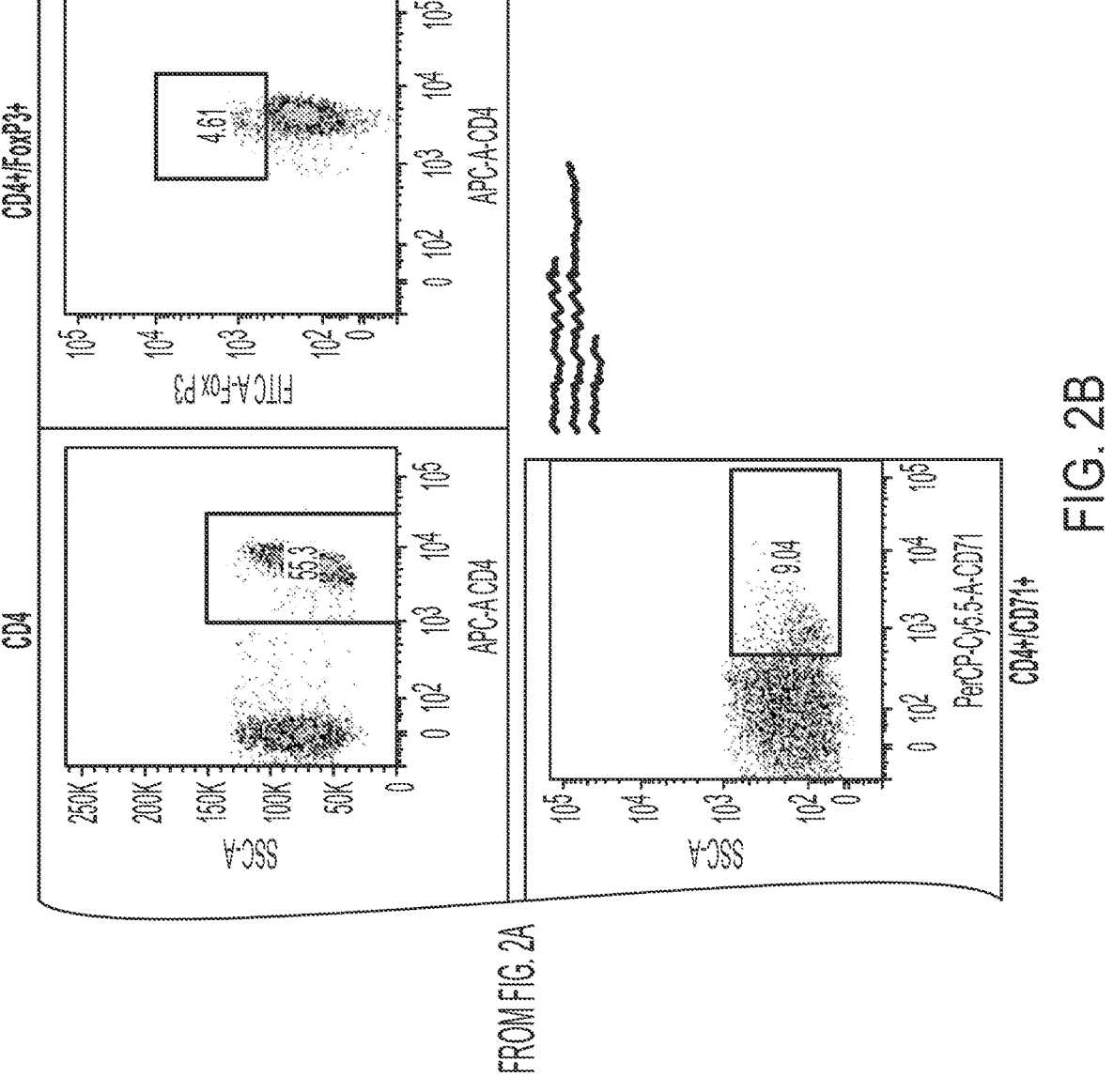
Figure 3A:
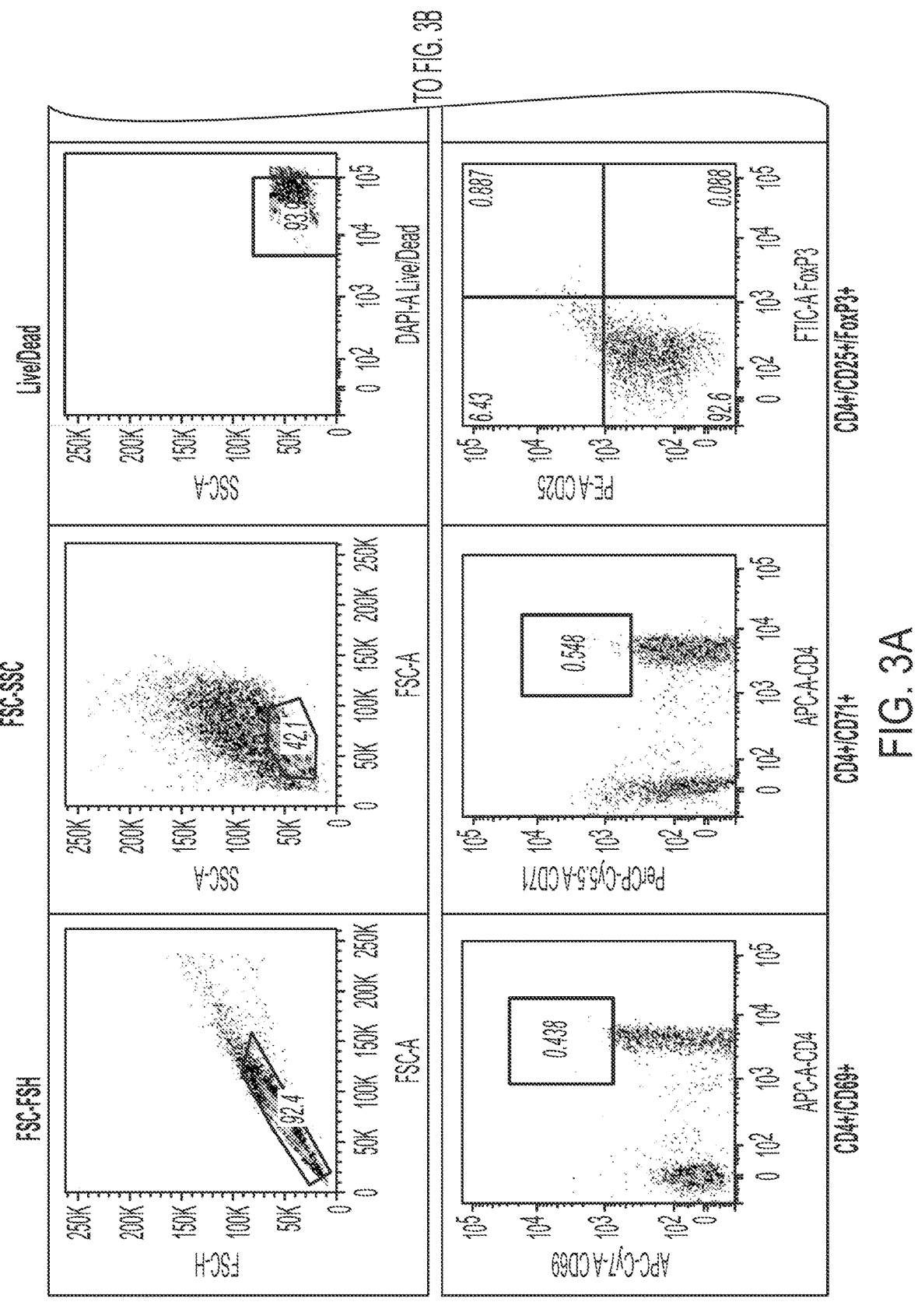
FIGS. 3A and 3B show flow cytometry plots showing staining for activation markers on T cells stimulated with 20 μg/mL of PHA.
Figure 3B:
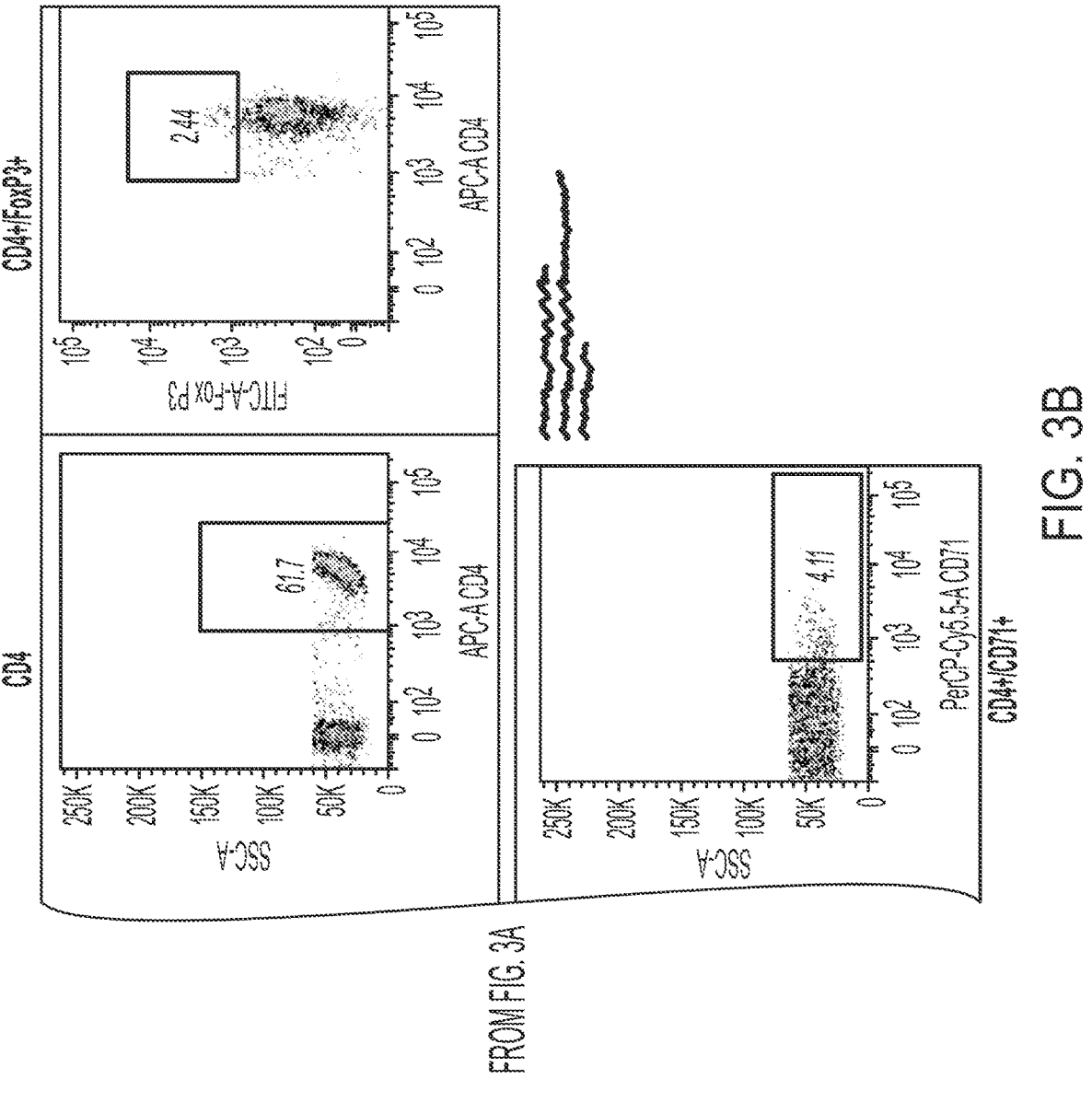
Figure 4A:
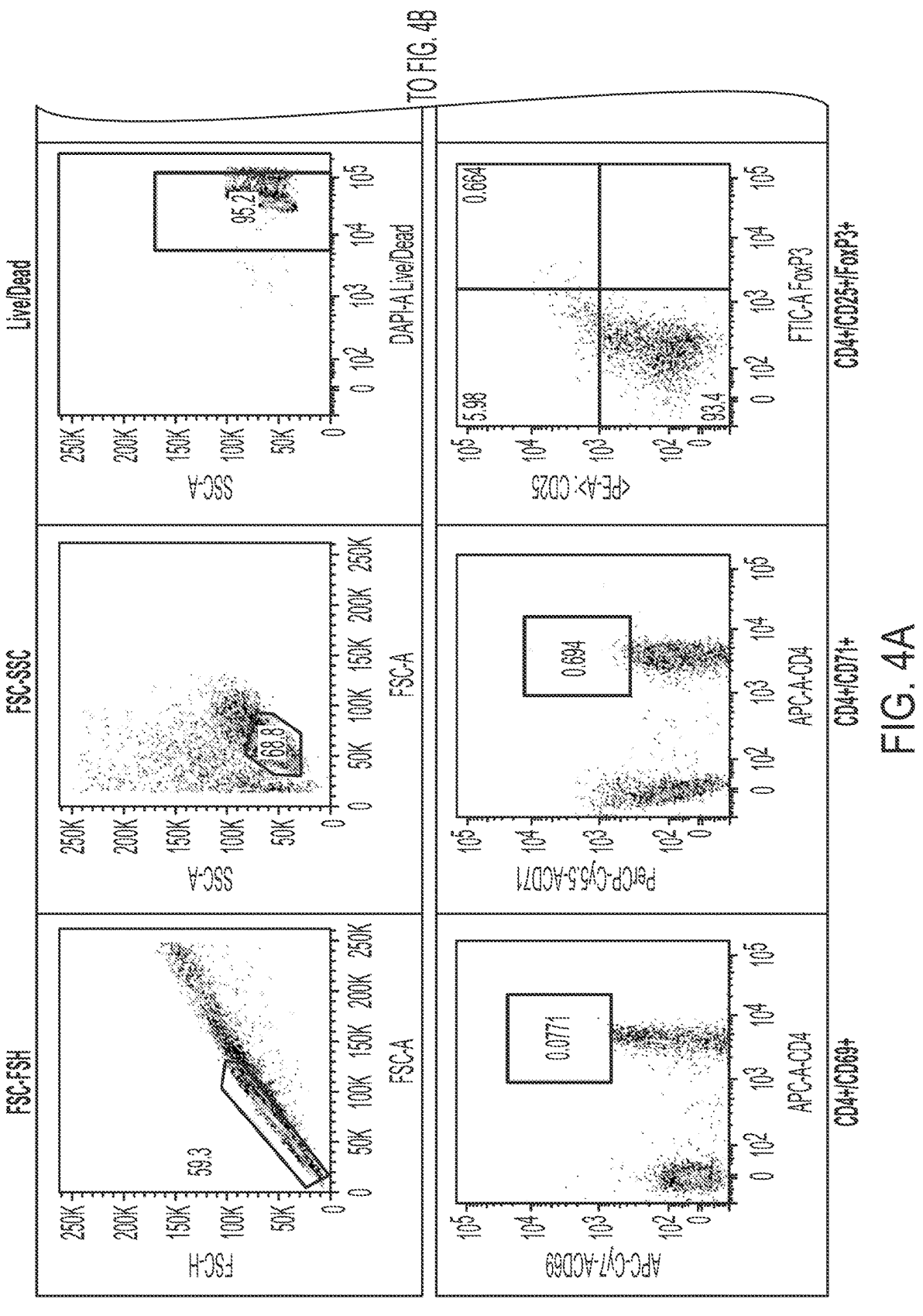
FIGS. 4A and 4B show flow cytometry plots showing staining for activation markers on T cells stimulated with 30 μg/mL of PHA.
Figure 4B:
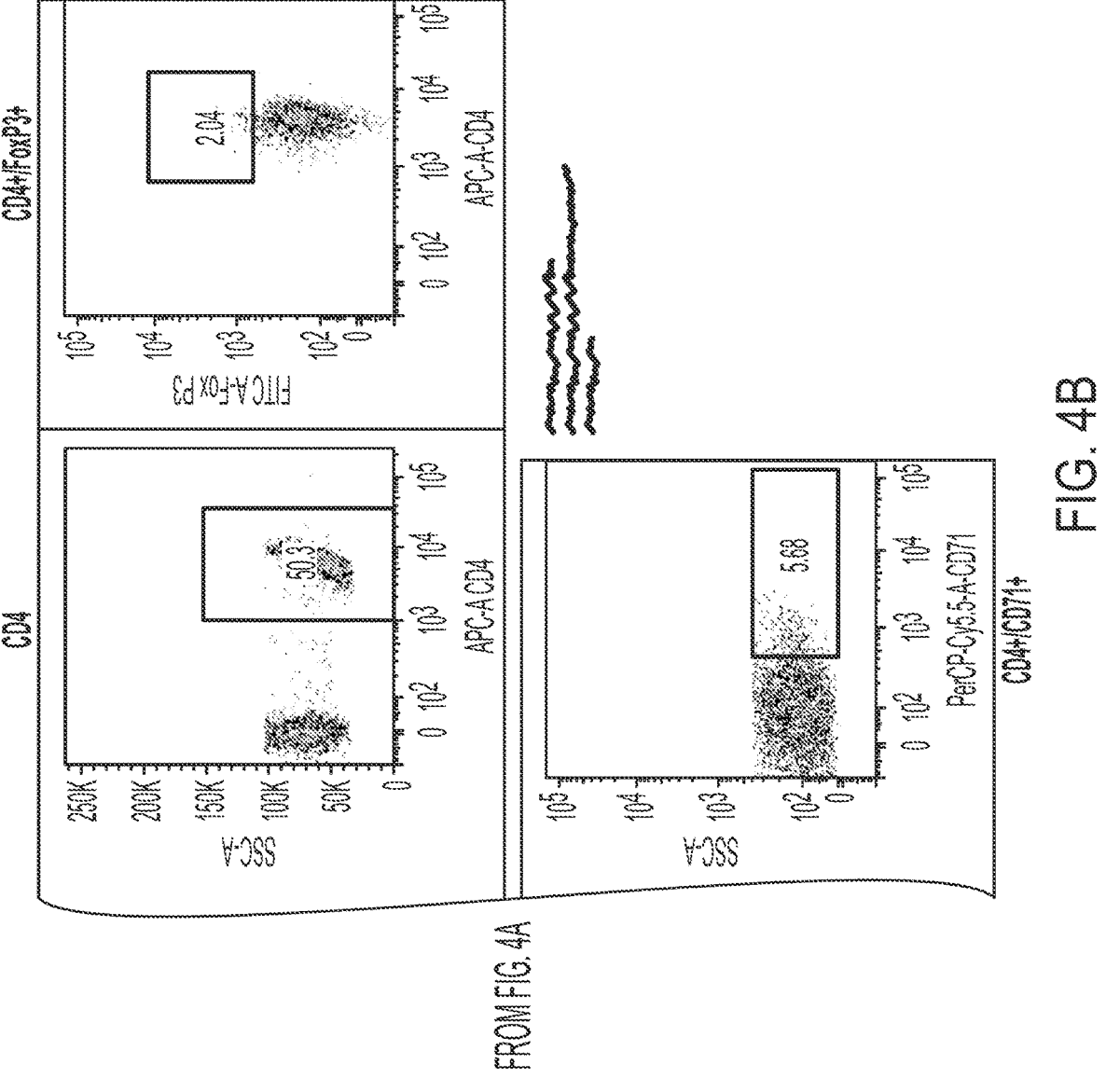

FIGS. 1A and 1B show the results of T cell activation marker screens on non-stimulated (no PHA) blood samples. As shown, the T cells in the non-stimulated samples did not show appreciable staining for any of Fox3, CD4, CD25, cD69, and CD71.

Figures 8A, 8B:
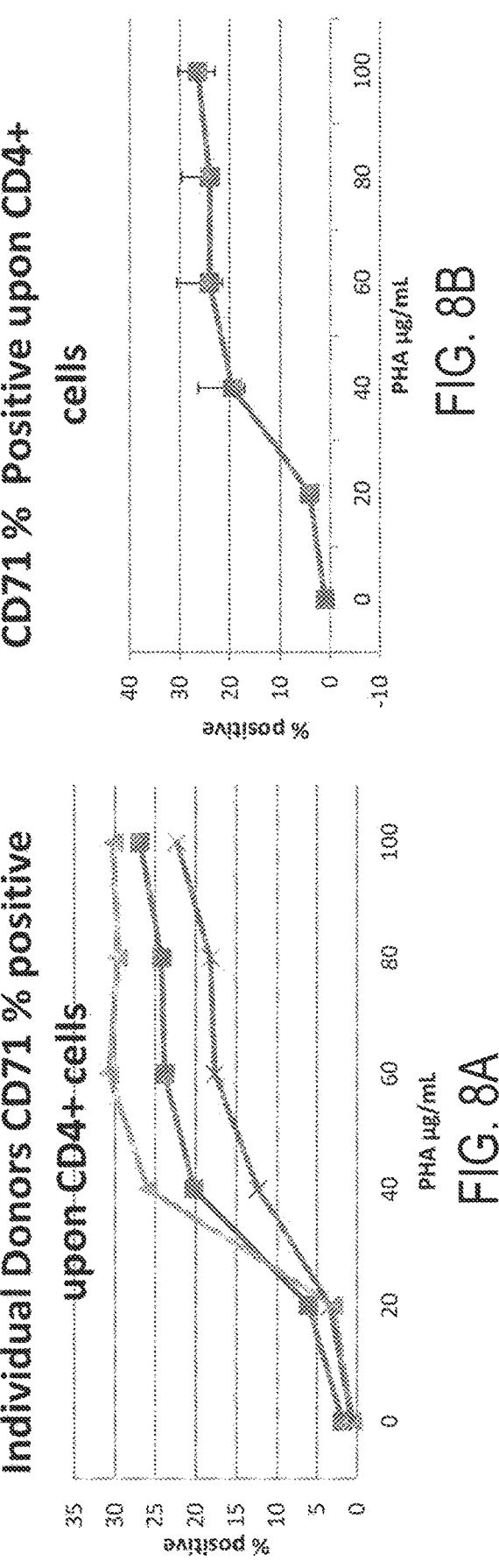
FIG. 8A shows the percentage of CD71-positive CD4+ T cells from the blood of three individual donors stimulated with increasing concentrations (0, 20, 470, 60, 80, 100 μg/mL) of PHA.
FIG. 8B shows the average percentage of CD71-positive CD4+ T cells from the donor pool, as stimulated with increasing concentrations (0, 20, 470, 60, 80, 100 μg/mL) of PHA.
Figures 9, 10A, 10B:
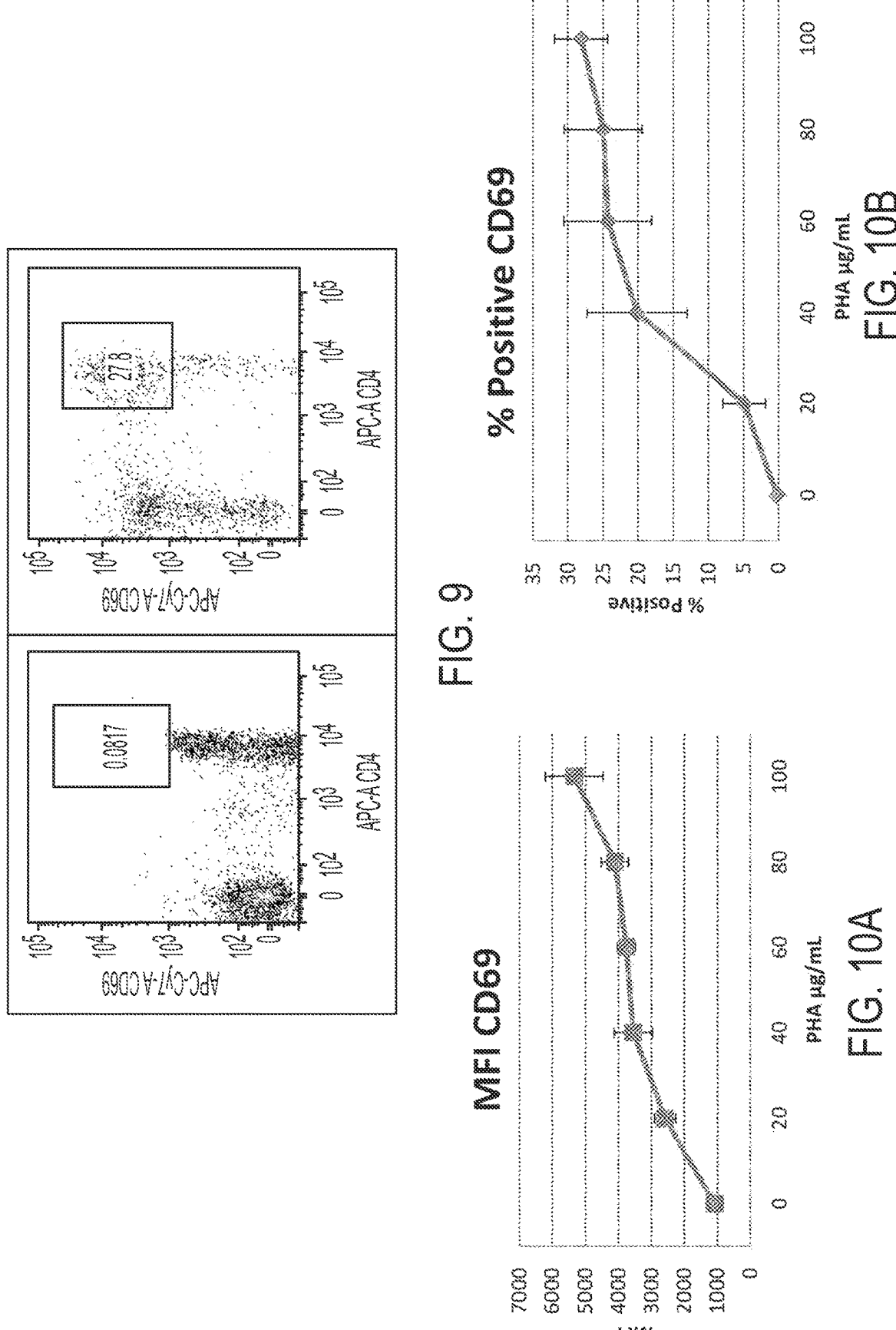
FIG. 9 shows activation of CD69+ T cells stimulated with 100 μg/mL PHA.
FIG. 10A shows the mean fluorescence intensity of CD69 staining in T cells from the donor pool as simulated with increasing concentrations (0, 20, 470, 60, 80, 100 μg/mL) of PHA.
FIG. 10B shows the average percentage of CD69-positive CD4+ T cells from the donor pool, as stimulated with increasing concentrations (0, 20, 470, 60, 80, 100 μg/mL) of PHA.

FIGS. 2A-2B, 3A-3B and 4A-4B show the results of T cell activation marker screens on PHA-stimulated blood samples, based on increasing concentrations of PHA (FIG. 8 shows results of cell stimulation with 10 μg of PHA, FIG. 9 shows results of cell stimulation with 20 μg of PHA, and FIG. 10 shows results of cell stimulation with 30 μg of PHA). As shown, PHA induces a substantial increase in CD4 expression on the T cells, and further induces a significant increase in the expression of CD25, CD69, CD71, and FoxP3 on the T cells.

Figure 5:
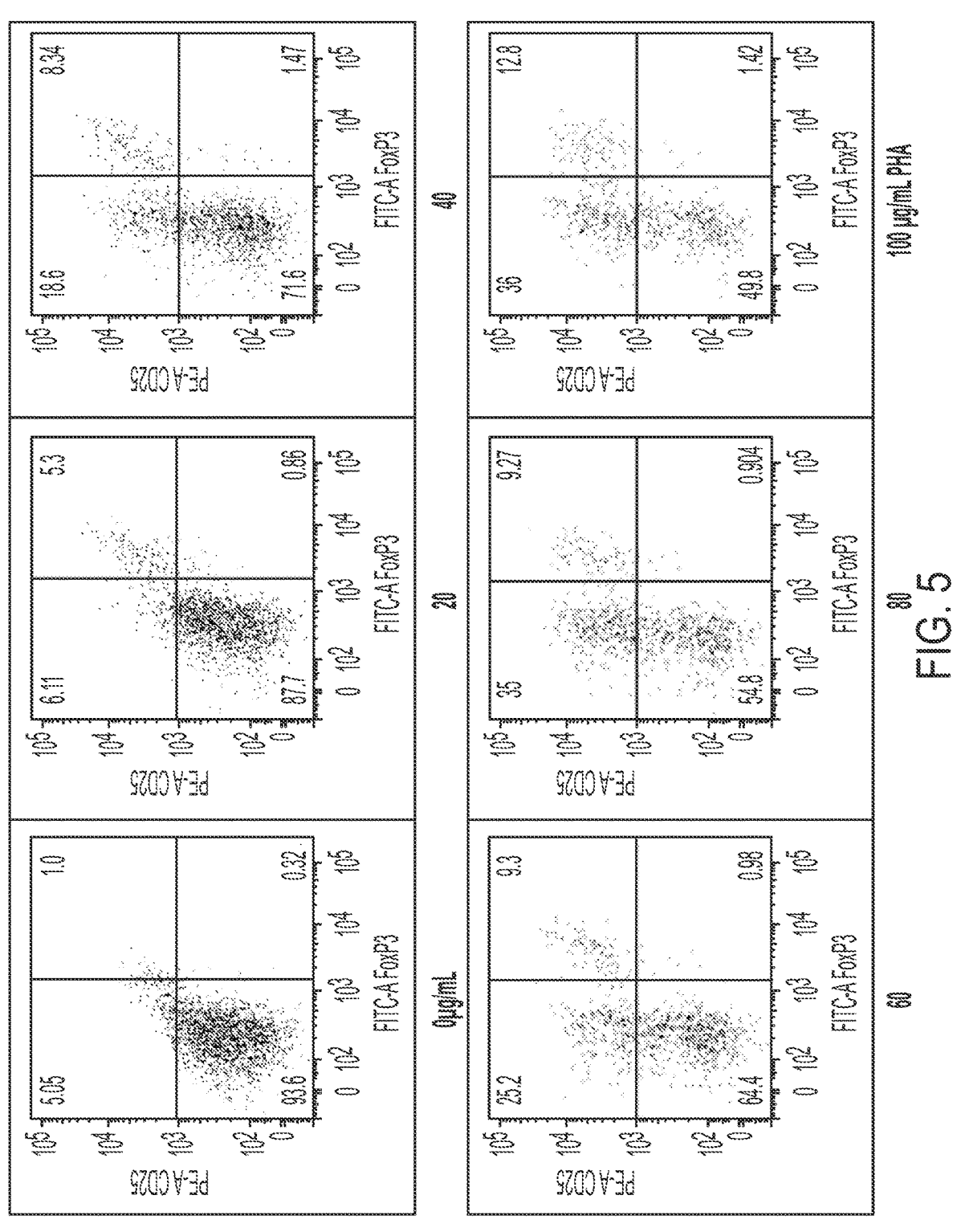
FIG. 5 shows activation of FoxP3+/CD25+ upon CD4+ T cells stimulated with increasing concentrations (0, 20, 470, 60, 80, 100 μg/mL) of PHA.
Figures 6A, 6B:
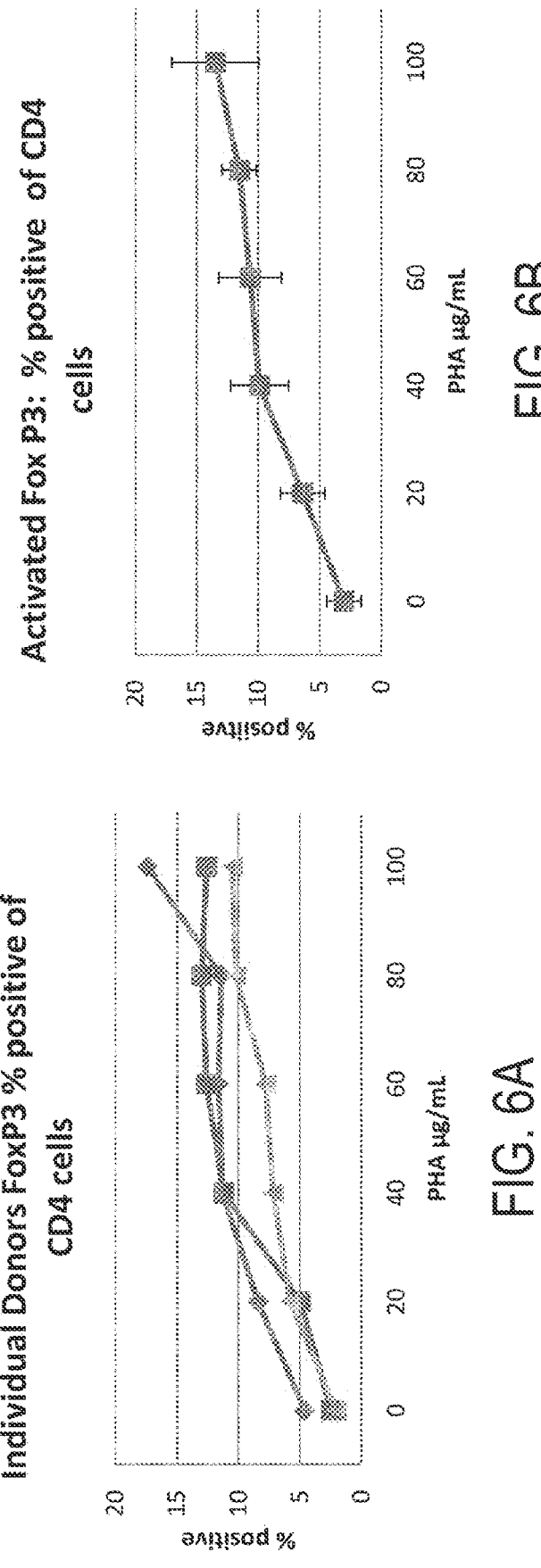
FIG. 6A shows the percentage of FoxP3-positive CD4+ T cells from the blood of three individual donors stimulated with increasing concentrations (0, 20, 470, 60, 80, 100 μg/mL) of PHA.
FIG. 6B shows the average percentage of FoxP3-positive CD4+ T cells from the donor pool, as stimulated with increasing concentrations (0, 20, 470, 60, 80, 100 μg/mL) of PHA.

FIGS. 5, 6A, and 6B show the enhancement of the level of FoxP3 expression on CD4+ cells with increasing amounts of PHA (from 0 micrograms to 100 micrograms over 20 microgram increments). FIG. 12A graphs the percentage of FoxP3-positive CD4+ cells in select individual blood donors. FIG. 6B graphs the percentage of FoxP3-positive CD4+ cells in the pool of blood donors.

Figure 7:
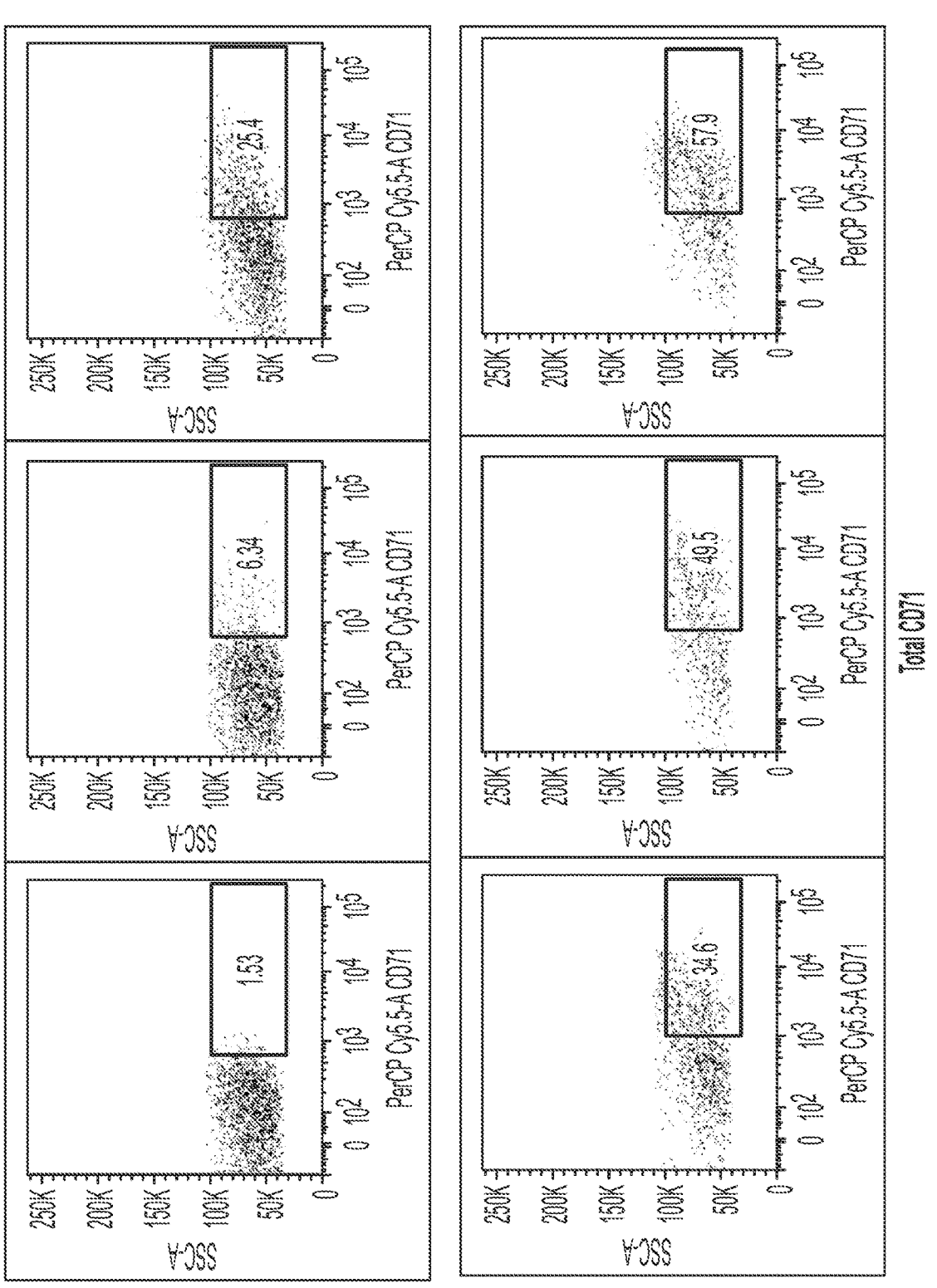
FIG. 7 shows activation of CD71+ T cells stimulated with increasing concentrations (0, 20, 470, 60, 80, 100 μg/mL) of PHA.

FIGS. 7, 8A, and 8B show the enhancement of the level of CD71 expression on CD4+ cells with increasing amounts of PHA (from 0 micrograms to 100 micrograms over 20 microgram increments—plots moving from left to right). FIG. 8A graphs the percentage of CD71-positive CD4+ cells in select individual blood donors. FIG. 8B graphs the percentage of CD71-positive CD4+ cells in the pool of blood donors.

FIGS. 9, 10A, and 10B show the enhancement of the level of CD69 expression on CD4+ cells with increasing amounts of PHA (from 0 micrograms (left) to 100 micrograms (right). FIG. 10A graphs the mean fluorescence intensity (MFI) of CD69 staining in the pool of blood donors over increasing amounts of PHA. FIG. 10B graphs the percentage of CD69–positive CD4+ cells in the pool of blood donors.

These data show that normal whole blood CD71, CD69, FoxP3 and CD25+ cells are stimulated by 20-100 ug/mL PHA. These experiments were repeated using a combination of CD3 and CD28 to stimulate T cells in the blood samples (PHA stimulation was run in parallel). The data showed that CD3/CD28 stimulation induced enhanced expression of CD4, CD25, CD69, CD71, and FoxP3 at levels similar to PHA stimulation (data not shown). Although the present disclosure has largely been described in connection with a flow cytometer for providing test results related to a blood sample, the present disclosure contemplates alternative analytical systems for providing such test results, for example, fluorescent microscope based systems.

The present disclosure is not limited to the embodiments described and exemplified above, but is capable of variation and modification within the scope of the appended claims.

Various publications, including patents, published applications, technical articles and scholarly articles are cited throughout the specification. Each of these cited publications is incorporated by reference herein, in its entirety and for all purposes.

OTHER EMBODIMENTS AND EQUIVALENTS

While the present disclosure has explicitly discussed certain particular embodiments and examples of the present disclosure, those skilled in the art will appreciate that the disclosure is not intended to be limited to such embodiments or examples. On the contrary, the present disclosure encompasses various alternatives, modifications, and equivalents of such particular embodiments and/or example, as will be appreciated by those of skill in the art.

Accordingly, for example, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

What is claimed is:

1. A kit for determining a presence of a pathogen in a subject, the kit comprising:

one or more antigens of the pathogen; and a plurality of test tubes, each of the plurality of test tubes comprising an interior wall and having the one or more antigens of the pathogen coated on the interior wall, wherein when a biological sample obtained from the subject is exposed to the one or more antigens of the pathogen for a period of time sufficient to activate responding immune cells if the pathogen is present in the sample, the one or more antigens activate the responding immune cells to the pathogen in the sample;

a first container comprising a first reagent, the first reagent comprising a first detectably-labeled antibody configured to bind to at least one activation marker of the responding immune cells in the sample; and a second container comprising a second reagent, the second reagent comprising a second detectably-labeled antibody configured to bind to one or more cytokines and/or chemokines secreted from the responding immune cells in the sample, wherein the labels of the first detectably-labeled antibody and the second detectably-labeled antibody are different.

2. The kit of claim 1, further comprising one or more additional containers, the one or more additional containers configured to hold at least one of a plurality of additional reagents.

3. The kit of claim 1, further comprising reference samples, or reference levels thereof, that have not been exposed to the pathogen, for determining whether measured levels of the first detectably-labeled antibody bound to the at least one activation marker and the second detectably-labeled antibody bound to the one or more cytokines and/or chemokines of the responding immune cells in the biological sample obtained from the subject are elevated relative to the reference samples, or reference levels thereof, that have not been exposed to the pathogen.

4. The kit of claim 1, further comprising instructions for processing the biological sample obtained from the subject, instructions for performing a test, instructions for interpreting results, or combinations thereof.

5. The kit of claim 1, wherein the one or more antigens of the pathogen coated on the interior wall of each of the plurality of test tubes is suspended in liquid phase when the biological sample is exposed to the one or more antigens of the pathogen.

* * * * *